(12) United States Patent
Frigg

(10) Patent No.: US 6,406,234 B2
(45) Date of Patent: Jun. 18, 2002

(54) BLIND RIVET WITH FASTENER

(75) Inventor: Robert Frigg, Bettlach (CH)

(73) Assignee: Synthes (USA), Paoli, PA (US)

(*) Notice: Subject to any disclaimer, the term of this patent is extended or adjusted under 35 U.S.C. 154(b) by 0 days.

(21) Appl. No.: 09/729,077

(22) Filed: Dec. 4, 2000

Related U.S. Application Data

(63) Continuation of application No. PCT/CH99/00194, filed on May 11, 1999.

(51) Int. Cl.⁷ .............................. F16B 13/04; F16B 13/06
(52) U.S. Cl. ............................ 411/42; 411/43; 411/45; 411/55; 411/69; 606/63
(58) Field of Search ................. 411/42, 43, 45, 411/51, 52, 53, 55, 69; 606/63

(56) References Cited

U.S. PATENT DOCUMENTS

| | | | | |
|---|---|---|---|---|
| 2,885,798 A | * | 5/1959 | Palmer et al. ............ | 411/43 X |
| 3,515,028 A | * | 6/1970 | Patton ..................... | 411/42 |
| 4,170,920 A | | 10/1979 | Siebol | |
| 4,580,936 A | | 4/1986 | Francis et al. ............ | 411/38 |
| 4,696,610 A | | 9/1987 | Wright .................... | 411/38 |
| 4,736,560 A | | 4/1988 | Murphy ................... | 52/410 |
| 4,897,003 A | * | 1/1990 | Bradley et al. ........... | 411/43 |
| 4,909,687 A | * | 3/1990 | Bradley et al. ........... | 411/43 |

FOREIGN PATENT DOCUMENTS

| | | |
|---|---|---|
| DE | 27 01 279 A1 | 7/1977 |
| DE | 32 17 065 A1 | 11/1983 |
| EP | 0 328 314 A2 | 8/1989 |
| EP | 0 537 967 A1 | 4/1993 |
| EP | 0 747 023 A1 | 12/1996 |
| FR | 2141020 | 1/1973 |
| GB | 887799 | 1/1962 |
| GB | 2 054 082 A | 2/1981 |

* cited by examiner

Primary Examiner—Neill Wilson
(74) Attorney, Agent, or Firm—Pennie & Edmonds, LLP

(57) ABSTRACT

The present invention relates to an orthopedic fastener for fixing an implant, suture, or tissue to a bone. The fastener comprises a blind rivet and a closing element. The blind rivet includes a head at a proximal end, a shank connected to the head, and an anchoring portion near a distal end. A bore extends through the head and shank from the proximal end to the distal end and the bore has a polygonal cross-section through the anchoring portion. The closing element has a body with an outer surface and is configured and dimensioned to be received in the anchoring portion. The outer surface of at least a portion of the closing element distal end has a polygonal cross-section flaring along the longitudinal axis toward the closing element distal end. The anchoring portion of the blind rivet severs into a plurality of anchoring legs when the closing element is pulled in the bore toward the blind rivet proximal end to thereby prevent rotation of the fastener.

23 Claims, 3 Drawing Sheets

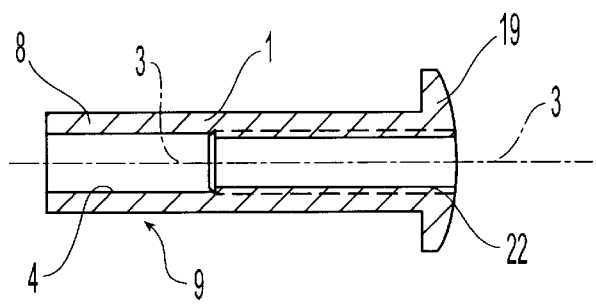
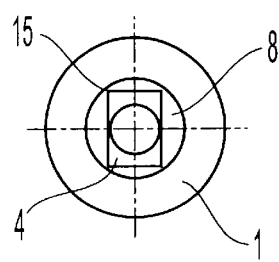
Fig. 6   Fig. 7
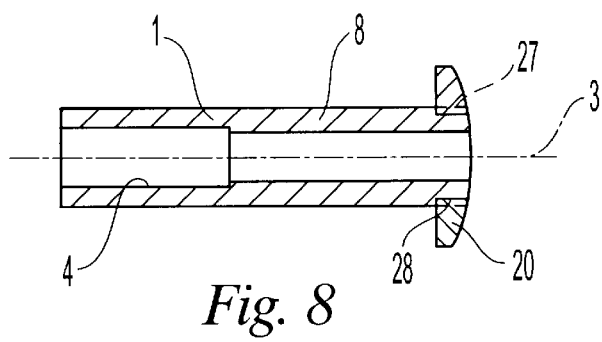
Fig. 8
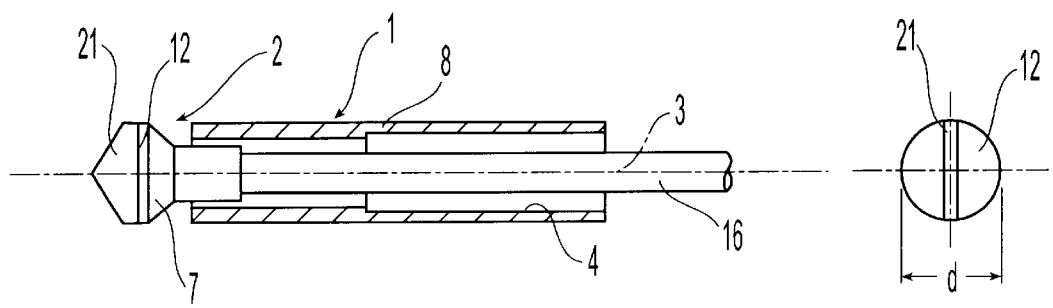
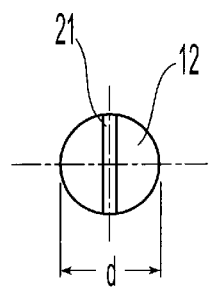
Fig. 9   Fig. 10

BLIND RIVET WITH FASTENER

CROSS-REFERENCE TO RELATED APPLICATIONS

This application is a continuation of the U.S. National Stage designation of International Patent Application PCT/CH99/00194, filed on May 11, 1999, which claims priority to International Patent Application PCT/CH98/00242, filed Jun. 4, 1998. The entire content of both these applications is expressly incorporated herein by reference thereto.

FIELD OF THE INVENTION

The present invention relates to a device for attaching a suture, tissue, or implant to a bone.

BACKGROUND OF THE INVENTION

The use of blind rivets in non-medical fields is widespread. Such blind rivets, which typically have a closing head consisting of separate and comparatively widely spread legs, are known for example from U.S. Pat. No. 4,696,610 to Wright and U.S. Pat. No. 4,580,936 to Francis. These known blind rivets have longitudinal slits or cuts near the end of the shaft which form the closing head when the blind rivet is closed. The closing heads so formed rest on a large area. These known blind rivets incur the drawback that the closing heads are formed by bending the longitudinal legs and, as a result, the leg ends are not sharp tines and cannot be pressed into the material to which the rivet is being attached. Thus, these types of blind rivets do not prevent the blind rivet from rotating in the boreholes of the materials to be connected.

A different non-medical blind rivet is known from British Application No. 2,054,082 of Tucker Fasteners. This fastener includes a pyramidal shaped head that passes through a cylindrical bore.

Other fasteners operate in a manner analogous to a blind rivet. Examples of these fasteners include screws, marrow pins, and hip screws. The Seidel marrow pin for the humerus is fitted with slits at the tip and the slits are spread apart by a central pin with a ballhead. In this manner, the legs are bent outward like wings. However, these legs are bent only slightly away from the nail. Use of these fasteners to anchor an implant in porotic bone is problematic. Often an implant can be affixed to such bone only by injecting bone cement into the bone. This procedure can further damage a bone due to heat necrosis as the cement hardens. Moreover, the cement no longer can be removed as would be required in case of infection.

Another drawback of these known fasteners is that the anchoring strength is determined by its diameter. If there is axial overload, a cylinder of bone equal to the fastener diameter will be torn out. In healthy bone, the anchoring strength of bone screws will be sufficient. But in the case of osteoporosis, in joint zones, or as regards thin, shell-like bones, screw affixation often will be inadequate. Larger screws cannot be used because of lack of space, or else they destroy the remaining bone even more.

Thus, there exists a need for an improved fastener.

SUMMARY OF THE INVENTION

The present invention relates to an orthopedic fastener for fixing an implant, suture, or tissue to a bone. The fastener comprises a blind rivet and a closing element. The blind rivet includes a head at a proximal end, a shank connected to the head, and an anchoring portion near a distal end. A bore extends through the head and shank from the proximal end to the distal end and the bore has a polygonal cross-section through the anchoring portion. The closing element has a body with an outer surface and is configured and dimensioned to be received in the anchoring portion. The outer surface of at least a portion of the closing element distal end has a polygonal cross-section flaring along the longitudinal axis toward the closing element distal end. The anchoring portion of the blind rivet severs into a plurality of anchoring legs when the closing element is pulled in the bore toward the blind rivet proximal end to thereby prevent rotation of the fastener.

The anchoring legs can be spread by the closing elements into a semi-circular shape relative to the longitudinal axis to thereby form the closing head of the blind rivet. This feature provides a broad rest for instance on the inside bone surface and, because the semi-circular shape of the anchoring leg ends rest almost perpendicularly on the bone surface, this design offers jaw-like anchoring the closing head. The blind rivet can be made of a plastically deforming material, such as pure titanium, a titanium alloy, or implant-steel, to enhance the formation of the semi-circular anchoring legs.

In another embodiment of the fastener of the invention, two mutually opposite ends of two mutually opposite anchoring legs of the closing element subtend a distance "L" which is two to three times the blind rivet's diameter "D". Again this considerable widening of the anchoring legs provides a broad rest on the inside bone surface.

The polygonal cross-section of the bore can include a plurality of corners that form rupture sites between the corner and the outer diameter of the shank to facilitate severing of the anchoring portion into the anchoring legs. In an exemplary embodiment, the rupture sites have a wall thickness between about 1% and 9% of the outside diameter of the shank.

The head of the blind rivet can be integral with the shank. Alternatively, the head of the blind rivet is detachable from the shank. If detachable, the rivet head can include an inside thread and the shank includes a matching outside thread for detachable coupling of the head and shank.

The closing element distal end can have a conical cross-section. The distal end of the closing element can also have a tip (like a gimlet or awl) for facilitating insertion of the closing element in bone. In order to facilitate severing, the anchoring portion can have a wall thickness that is between about 1% and 20% of the outer diameter of the shank. This design allows spreading the rivet shank in simple manner into the separate anchoring elements by means of the polygonal cone at the closing element. In one embodiment, the distal end has a wall thickness that is greater than that of the proximal end of the blind rivet.

In an exemplary embodiment, the fastener includes a closing pin operatively associated with the closing element. The closing pin has a first end extending through the bore to pull the closing element through the blind rivet toward the proximal end. The closing element can be detachably connected to the closing pin. For example, the closing pin can be connected to the closing element by a design rupture site which allows the closing pin to separate from the closing element. Alternatively, the proximal end of the closing element includes a thread and an end of the closing pin includes a matching thread.

The fastener according to the present invention results in palliation. In use, the fastener is insertable through a small borehole and, following affixation, includes a broad resting surface on the inner bone surface due to the spread out anchoring legs. These anchoring legs can dig into the inner bone surface and thereby prevent the blind rivet from rotating.

One advantage offered by the present invention is that the fastener of the invention requires only a small borehole in the bone. However, after implantation, the blind rivet of the invention broadly rests on the inner bone surface. Moreover and illustratively in a manner different from the case relating to a hip screw, the semicircular anchor-like design of the anchoring legs and their anchoring in the bone preclude rotation by the fastener head. With respect to porotic bones, the spongiosa in joint heads—if still present at all—will not be mechanically stressed. In other words, the hip screw is situated in a cavity, and this feature entails a dislocation of the hip head relative to the hip screw. The hip screw only can become functional after it makes contact with the inner bone surface. In such cases, however, the interface between screw and bone often is inadequate, so that the bone screw may penetrate the hip joint. In the invention on the other hand, the inner head surface is used as the interface between implant and bone when using the blind rivet of the invention with the semi-circular anchoring legs. In this manner, the surface of contact with the bone is larger and matches optimally on account of the anatomically matching anchoring legs. If the blind rivet of the invention is used to anchor a marrow spindle into the femur head, the size of the borehole receiving the blind rivet of the invention will only be about 8 mm. This feature offers the advantage that in comparison with conventional systems of marrow-spindles/hip-screws, the diameter of the marrow spindle can be substantially reduced in the application of the invention.

In the medical field, the fastener of the invention is applicable almost universally in the treatment of bone fractures for which a bone screw or similar fastener is presently used. Specifically:

for porotic bones partly comprising only a very thin cortex, the fastener of the invention can replace screws in fastening plates;

in the spongiosa, the fastener of the invention can serve as an anchor for plates, sutures or to reattach tendons and ligaments (the claws formed when spreading the closing head will anchor well into the trabecular structure of the spongiosa); and in joint heads such as the femur head or the humerus head, the fastener of the invention can be used as the anchor of a side plate or of an intramedullary support (heretofore large screws have been used to anchor the longitudinal supports, however these screws anchor less than optimally in the joint heads' porotic bones).

BRIEF DESCRIPTION OF THE DRAWINGS

FIG. 6 is a longitudinal section of another embodiment of the blind rivet component of the fastener according to the present invention;

FIG. 7 is a front view of the blind rivet shown in FIG. 6;

FIG. 8 is a longitudinal section of another embodiment of the blind rivet component of the fastener according to the present invention;

FIG. 9 is a longitudinal section of another embodiment of the fastener according to the present invention;

FIG. 10 is a front view of the fastener of FIG. 9; and

DETAILED DESCRIPTION OF DRAWINGS

Figure 1:
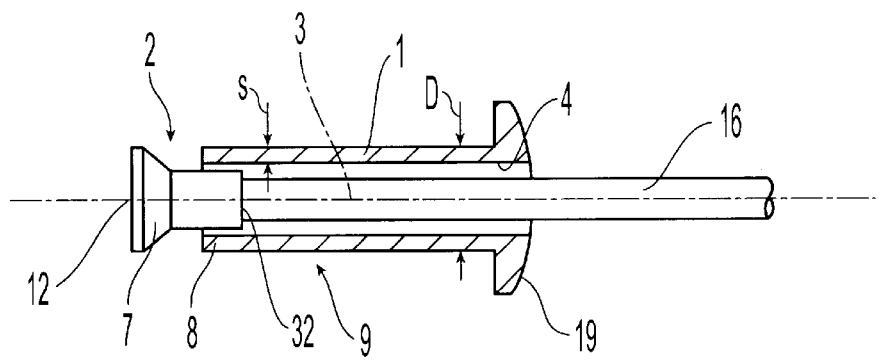
FIG. 1 shows a longitudinal section of an embodiment of a fastener according to the present invention.
Figure 3:
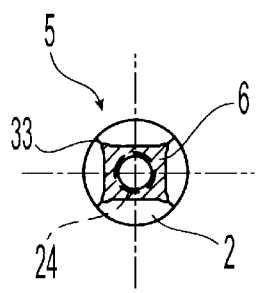
FIG. 3 is a cross-section taken along line I—I of FIG. 2.
Figure 4:
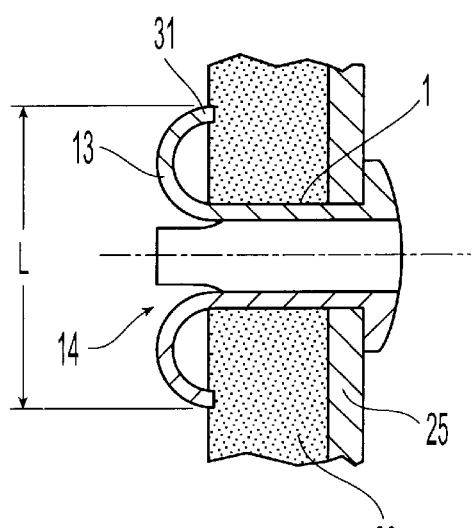
FIG. 4 is a longitudinal section of a fastener with a closed blind rivet fixing a bone plate to a bone.
Figure 5:
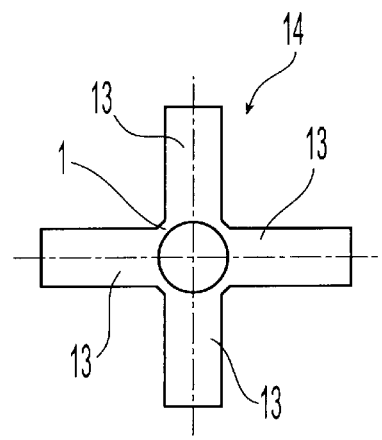
FIG. 5 is an elevation of the embodiment of the closed blind rivet shown in FIG. 4.

FIG. 1 shows one embodiment of the fastener according to the present invention. The fastener includes a blind rivet 1 and a closing element 2. Blind rivet 1 has a longitudinal axis 3 and consists of a cylindrical rivet shank 8 that runs parallel to longitudinal axis 3 and a rivet head 19 rigidly joined to rivet shank 8. A cylindrical passage (i.e., a bore) 4 passes coaxially through blind rivet 1. Rivet shank 8 is of diameter "D" and, as a result, the wall thickness "s", defined by the width of passage 4 and the outside diameter "D", is such that when closing blind rivet 1 by means of closing element 2, the blind rivet can be severed at the closing part or anchoring part 9 into anchoring legs 13 (FIG. 4 and FIG. 5). The number of anchoring legs 13 corresponds to the number of edges of the polygonal cross-section 5 of closing element 2 (FIG. 3). In this particular embodiment of blind rivet 1, wall thickness "s" of rivet shank 8 amounts to 14% of the outer diameter "D".

In the embodiment of the fastener of the invention shown in FIG. 1, closing element 2 is a component of a closing pin 16. At the segment adjoining rear end 12, closing element 2 is of polygonal cross-section 5 (FIG. 3) flaring toward rear end 12. Blind rivet 1 will be closed following insertion of closing element 2 which, by tension applied to closing pin 16, is pressed into closing part 9 of blind rivet 1. When flaring segment 7 is pressed inward, the wall of rivet shank 8 is widened by segment 7 of closing element 2 and is severed by the edges of polygonal cross-section 5 into anchoring legs 13. The conical angle being selected in such manner that both severing of the rivet shank into separate anchoring legs and widening of the anchoring legs when closing the blind rivet will be enhanced. Closing pin 16 can be connected by a design rupture site to closing element 2 to allow separating this pin from this closing element after closing blind rivet 1, for instance by applying twisting forces.

Figure 2:
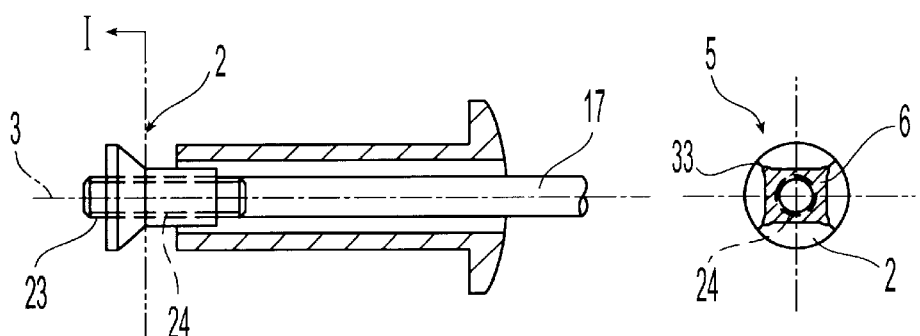
FIG. 2 shows a longitudinal section of a fastener according to the present invention with a closing element that differs from that of FIG. 1.

The embodiment of the fastener according to the present invention shown in FIG. 2 differs from the embodiment of FIG. 1 in that closing element 2 is fitted with an inside thread 24 coaxial with longitudinal axis 3 and closing pin 17 is fitted with a matching outside thread 23 to allow detachably screwing closing pin 17—which is a separate part—into closing element 2. Following closure of blind rivet 1, closing pin 17 can be screwed out of closing element 2 and thereby be removed from closed blind rivet 1.

FIG. 3 is a section perpendicular to the longitudinal axis of the closing element 2. In this embodiment, the polygonal cross-section 5 is a square 6 forming four anchoring legs 13 when closing blind rivet 1. FIG. 3 also shows inside thread 24 of closing element 2 of the fastener of the invention embodiment of FIG. 2.

FIG. 4 shows a longitudinal section of a closed blind rivet 1 of another embodiment of the invention. Blind rivet 1 connects a bone plate 25 to a bone 26. Cosing head 14 comprises four anchoring legs 13, of which ends 31 subtend the distance "L". FIG. 4 also shows that the distance "L"

subtended by ends 31 of anchoring legs 13 is approximately triple the diameter "D" of rivet shank 8. FIG. 5 shows an elevation of the closed blind rivet 1 of FIG. 4 with four anchoring legs 13.

The blind rivet 1 shown in FIG. 6 and FIG. 7 of another embodiment of the fastener of the invention differs from the embodiment of FIG. 1 in that bore 4 has a square cross section at closing part 9 of blind rivet 1. One advantage of a cross-section of few polygonal edges is that the edges are more sharply defined and severing the rivet shank into separate anchoring legs and widening these legs when closing the blind rivet is thus enhanced. Corners 15 of bore 4 form design rupture sites between this passage and the outside diameter "D" of rivet shank 8 to facilitate severing of shank 8 into anchoring legs 13 when blind rivet 1 is being closed. Advantageously, the rupturing sites wall thickness can be between 1% and 10%, and preferably between 5% and 9%, of the outside diameter "D" of the blind rivet. At the segment of the blind rivet 1 adjoining rivet head 19, bore 4 is fitted with an inside thread 22 coaxial with longitudinal axis 3.

The embodiment shown in FIG. 8 has a blind rivet 1 with a rivet head 20 that is detachably connected to rivet shank 8. This detachable connection of rivet head 20 and rivet shank 8 can be implemented by threads. Accordingly, river shank 8 is fitted with an outside thread 27 coaxial with longitudinal axis 3 and rivet head 20 is fitted with a matching inside thread 28.

FIG. 9 and FIG. 10 show a further embodiment of the fastener according to the present invention. Blind rivet 1 does not have a rivet head and consists of a cylindrical rivet shank 8 having a longitudinal axis 3 and a bore 4 also coaxial with axis 3. If the blind rivet is used as an anchor, for instance as a fastener in the femur head, together with a side plate or a marrow spindle or a suture anchor, an embodiment of the blind rivet without a rivet head will be appropriate. The design of a headless blind rivet offers the advantage of deeper bone penetration during spreading. This "post-slippage" prevents cutting the spongiosa when the blind rivet is being spread apart. Closing element 2 is fitted with an awl 21. The diameter "d" of awl 21 corresponds to the outside diameter "D" of the blind rivet 1 and thereby pre-drilling bone 26 (FIG. 4) is not needed when assembling blind rivet 1. A gimlet can be used instead of awl 21.

Figure 11:
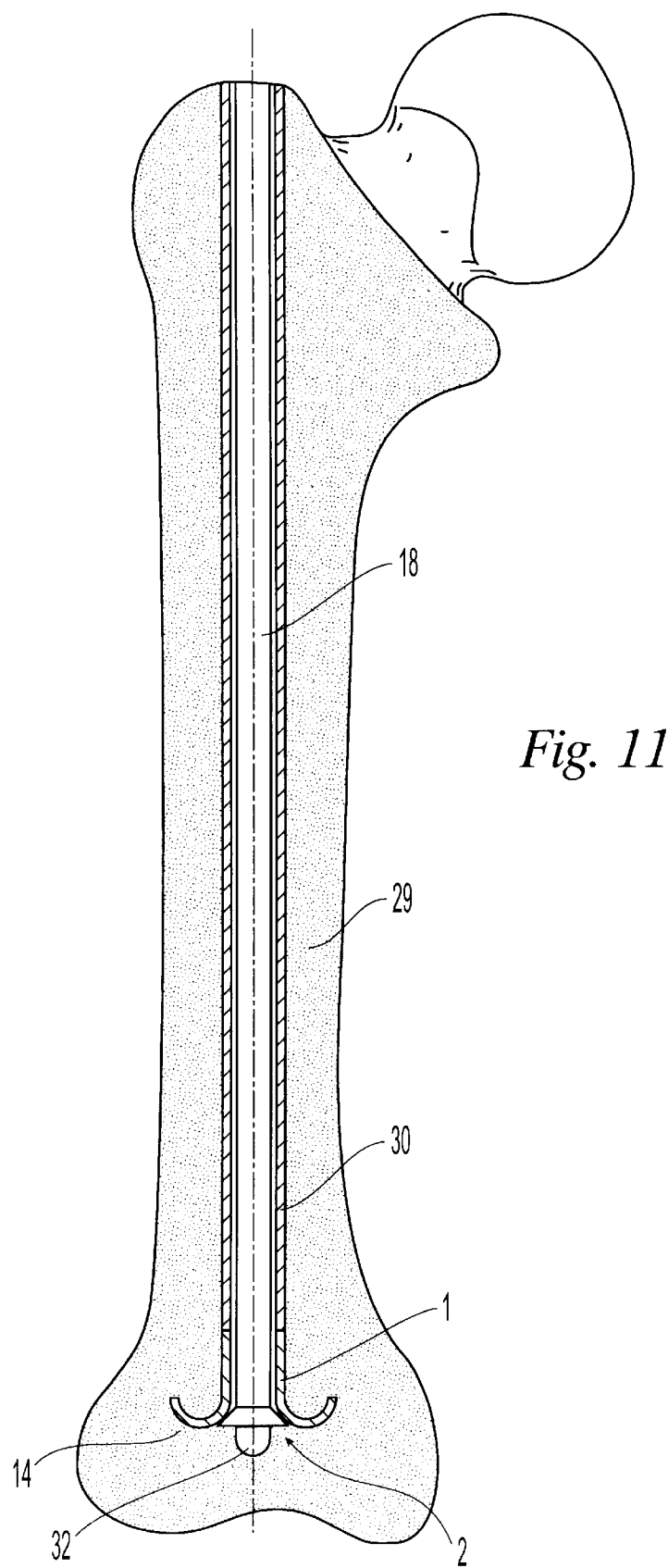
FIG. 11 is a longitudinal section of a femur bone with a marrow spindle, assembly sleeve, and a blind rivet according to the present invention.

FIG. 11 shows an application of blind rivet 1 to lock a marrow spindle 18 (for instance in a femur bone 29). Marrow spindle 18 is secured axially in the proximal direction by inserting blind rivet 1. Closing element 2 is mounted as a component of marrow spindle 18 at its distal end 32. To assemble blind rivet 1, it is clamped between closing element 2 and a case 30 and is inserted together with the marrow spindle 18 into the femur bone 29. By tensioning marrow spindle 18 in the proximal direction and applying an opposite retention force to case 30, closing head 14 is shaped at blind rivet 1, which thereby is locked.

The preferred embodiments disclosed above discuss the present invention using specific orthopedic procedures; however, the blind rivet can be used almost universally in the treatment of bone fractures where presently bone screws are used. While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the scope of the present invention.

What is claimed is:

1. An orthopedic fastener for fixing an implant, suture, or tissue to a bone, the fastener having a longitudinal axis and comprising:
    a blind rivet with proximal and distal ends and having a head at the proximal end, a shank connected to the head and including an outer diameter and an anchoring portion near the distal end, and a bore extending through the head and shank from the proximal end to the distal end, the bore having a polygonal cross-section through the anchoring portion; and
    a closing element having proximal and distal ends and a body with an outer surface and configured and dimensioned to be received in the anchoring portion, the outer surface of at least a portion of the closing element distal end has a polygonal cross-section flaring along the longitudinal axis toward the closing element distal end,
    wherein the anchoring portion of the blind rivet severs into a plurality of anchoring legs when the closing element is pulled in the bore toward the blind rivet proximal end to thereby prevent rotation of the fastener.

2. The fastener of claim 1 wherein the polygonal cross-section of the bore includes a plurality of corners that form rupture sites between the corner and the outer diameter of the shank to facilitate severing of the anchoring portion into the anchoring legs.

3. The fastener of claim 2 wherein the rupture sites have a wall thickness between about 1% and 9% of the outside diameter of the shank.

4. The fastener of claim 1 wherein the closing element distal end has a conical cross-section.

5. The fastener of claim 1 wherein the closing element is part of a marrow spindle.

6. The fastener of claim 1 wherein the head of the blind rivet is integral with the shank.

7. The fastener of claim 1 wherein the head of the blind rivet is detachable from the shank.

8. The fastener of claim 7 wherein the rivet head includes an inside thread and the shank includes a matching outside thread for detachable coupling of the head and shank.

9. The fastener of claim 1 wherein distal end of the closing element has a tip for facilitating insertion of the closing element in bone.

10. The fastener of claim 1 wherein at least a portion of the bore is threaded for threadably receiving an implant.

11. The fastener of claim 1 wherein the anchoring portion has a wall thickness that is between about 1% and 20% of the outer diameter of the shank.

12. The fastener of claim 11 wherein the distal end has a wall thickness that is greater than that of the proximal end of the blind rivet.

13. The fastener of claim 1 wherein two mutually opposite ends of two mutually opposite anchoring legs of the closing element subtend a distance two to three times the outer diameter of the shank.

14. The fastener of claim 1 further comprising a closing pin operatively associated with the closing element and having a first end extending through the bore to pull the closing element through the blind rivet toward the proximal end.

15. The fastener of claim 14 wherein the closing element is detachably connected to the closing pin.

16. The fastener of claim 15 wherein the closing pin is connected to the closing element by a design rupture site which allows the closing pin to separate from the closing element.

17. The fastener of claim 15 wherein the proximal end of the closing element includes a thread and an end of the closing pin includes a matching thread.

18. An orthopedic fastener for fixing an implant, suture, or tissue to a bone, the fastener having a longitudinal axis and comprising:

a blind rivet with proximal and distal ends and having a head at the proximal end, a shank connected to the head and including an outer diameter and an anchoring portion near the distal end, and a bore extending through the head and shank from the proximal end to the distal end, the bore having a polygonal cross-section through the anchoring portion; and a closing element having proximal and distal ends and a body with an outer surface and configured and dimensioned to be received in the anchoring portion, the outer surface of at least a portion of the closing element distal end has a polygonal cross-section flaring along the longitudinal axis toward the closing element distal end, wherein the anchoring portion of the blind rivet severs into a plurality of anchoring legs when the closing element is pulled in the bore toward the blind rivet proximal end to thereby prevent rotation of the fastener and wherein two mutually opposite ends of two mutually opposite anchoring legs of the closing elements subtend a distance two to three times the outer diameter of the shank.

19. The fastener of claim 18 wherein the polygonal cross-section of the bore includes a plurality of corners that form rupture sites between the corner and the outer diameter of the shank to facilitate servering of the anchoring portion into the anchoring legs.

20. The fastener of claim 18 wherein the distal end of the closing element has a tip for facilitating insertion of the closing element in bone.

21. An orthopedic fastener for fixing an implant, suture, or tissue to a bone, the fastener having a longitudinal axis and comprising:

a blind rivet with proximal and distal ends and having a head at the proximal end, a shank connected to the head and including an outer diameter and an anchoring portion near the distal end, and a bore extending through the head and shank from the proximal end to the distal end, the bore having a polygonal cross-section through the anchoring portion; and a closing element having proximal and distal ends and a body with an outer surface and configured and dimensioned to be received in the anchoring portion, the outer surface of at least a portion of the closing element distal end has a polygonal cross-section flaring along the longitudinal axis toward the closing element distal end, wherein the anchoring portion of the blind rivet severs into a plurality of anchoring legs when the closing element is pulled in the bore toward the blind rivet proximal end to thereby prevent rotation of the fastener, and wherein the head of the blind rivet is detachable from the shank.

22. The fastener of claim 21 wherein the rivet head includes an inside thread and the shank includes a matching outside thread for detachable coupling of the head and shank.

23. The fastener of claim 21 wherein the closing element is part of a marrow spindle.

* * * * *